(12) United States Patent
Tripodi et al.

(10) Patent No.: US 8,969,804 B2
(45) Date of Patent: Mar. 3, 2015

(54) DEVICE FOR ANALYZING A SAMPLE USING RADIATION IN THE TERAHERTZ FREQUENCY RANGE

(75) Inventors: Lorenzo Tripodi, Eindhoven (NL); Jaime Gomez Rivas, Eindhoven (NL); Ullrich Richard Rudolf Pfeiffer, Kreuztal (DE); Peter Gunther Haring Bolivar, Wenden (DE)

(73) Assignee: Koninklijke Philips N.V., Eindhoven (NL)

( * ) Notice: Subject to any disclaimer, the term of this patent is extended or adjusted under 35 U.S.C. 154(b) by 336 days.

(21) Appl. No.: 13/578,778

(22) PCT Filed: Feb. 7, 2011

(86) PCT No.: PCT/IB2011/050511
§ 371 (c)(1),
(2), (4) Date: Aug. 13, 2012

(87) PCT Pub. No.: WO2011/098943
PCT Pub. Date: Aug. 18, 2011

(65) Prior Publication Data
US 2012/0305772 A1    Dec. 6, 2012

(30) Foreign Application Priority Data
Feb. 15, 2010   (EP) .................................... 10153566

(51) Int. Cl.
*G01J 5/20*    (2006.01)
*G01N 21/3581*    (2014.01)
(Continued)

(52) U.S. Cl.
CPC .......... *G01N 21/3581* (2013.01); *G01N 21/553* (2013.01); *G01N 21/3563* (2013.01); *G02B 6/1226* (2013.01)

USPC ........................................................ 250/338.4
(58) Field of Classification Search
CPC .................................................. G01N 21/3581
USPC ........................................................ 250/338.4
See application file for complete search history.

(56) References Cited

U.S. PATENT DOCUMENTS 6,747,736 B2    6/2004    Takahashi
7,488,940 B2 *  2/2009    Ohtake et al. ............... 250/341.3
(Continued)

FOREIGN PATENT DOCUMENTS

DE    10054476 A1    1/2002
JP    2007078621 A   3/2007
(Continued)

OTHER PUBLICATIONS

Li et al. Terahertz surface plasmon polaritons on a semiconductor surface structured with periodic V-grooves, Mar. 25, 2013, Optics Express, vol. 21, pp. 7041-7049.*

(Continued)

*Primary Examiner* — Christine Sung

(57) ABSTRACT

A device for analyzing a sample using radiation in the terahertz frequency range is provided. The device comprises a transmitter (3) comprising a THz signal generator (5, 6, 7; 51) for generating an electromagnetic THz signal, the THz signal generator comprising a nonlinear transmission line (7; 52). The device further comprises a surface plasmon polariton generating unit (8) adapted to convert the THz signal into a surface plasmon polariton. The transmitter (3) and the surface plamon polariton generating unit (8) are either integrated on one common substrate or on two separate substrates.

13 Claims, 3 Drawing Sheets

(51) Int. Cl.
*G01N 21/552* (2014.01)
*G01N 21/3563* (2014.01)
*G02B 6/122* (2006.01)

(56) References Cited

U.S. PATENT DOCUMENTS

| | | | |
|---|---|---|---|
| 7,550,734 B1* | 6/2009 | Lee et al. | 250/370.12 |
| 2005/0231796 A1 | 10/2005 | Reed | |
| 2007/0008048 A1 | 1/2007 | Kintis | |
| 2008/0217538 A1 | 9/2008 | Ouchi | |
| 2010/0033709 A1 | 2/2010 | Lampin | |
| 2010/0322373 A1* | 12/2010 | Churilla | 378/4 |
| 2012/0019901 A1* | 1/2012 | Mazumder | 359/320 |
| 2013/0301983 A1* | 11/2013 | Mazumder et al. | 385/16 |

FOREIGN PATENT DOCUMENTS

| | | |
|---|---|---|
| WO | 2006123153 A1 | 11/2006 |
| WO | 2008105888 A2 | 9/2008 |
| WO | 2009013681 A1 | 1/2009 |

OTHER PUBLICATIONS

Kuttge et al., Terahertz Surface Plasmon Polaritons on Metal and Semiconductor Surfaces, 2004, IEEE, pp. 545, 546.*
Williams et al., Highly confined guiding of terahertz surface plasmon polaritons on structured metal surfaces, Mar. 2008, Nature photonics, vol. 2, pp. 175-179.*
Ricketts et al., A Chip Scale Electrical Soliton Modelocked Oscillator, 2006, IEEE International Solid-State Circuits Conference, pp. 1-10.*
Gomez Rivas et al., Propagation of Surface Plasmon Polaritons on Semiconductor Gratings, Dec. 17, 2004, Physical Review Letters, vol. 93, pp. 256804-1 to 256804-4.*
Isaac et al., Terahertz Surface Plasmons for Subwavelength Sensing and Spectroscopy, 2008, IEEE, pp. 10-12.*
Heshmat et al., Nanoplasmonic Terahertz Photoconductive Switch on GaAs, Nov. 21, 2012, Nano-Letters, vol. 12, pp. 6255-6259.*
Bostak, J.S. et al "All-Electronic Terahertz Spectroscopy System with Terahertz Free-Space Pulses", Journal of the Optical Society of America, B, vol. 11, No. 12, Dec. 1994, pp. 2561-2565.
Isaac, Tom H. et al "Terahertz Surface Plasmons for Subwavelength Sensing and Spectroscopy" THZ Radiiation; Basic Research and Applications, TERA 2008, pp. 10-12.
Van Der Weide, D.W., "Delta-Doped Schottky Diode Nonlinear Transmission Lines for 480-fs, 3.5-V Transients", Applied Physics Letters, vol. 65, Aug. 1994, pp. 881-883.
Saxler, J. et al "Time-Domain Measurements of Surface Plasmon Polaritons in the Terahertz Frequency Range", Physical Review B, vol. 69, No. 155427, 2004.
Rivas, J. Gomez et al "Propagation of Surface Plasmon Polaritons on Semiconductor Gratings", Physical Review Letters, vol. 93, 256804, 2004.
Marsland, R.A. et al "Monolithic Integrated Circuits for MM-Wave Instrumentation", IEEE GaAs IC Symposium, Oct. 1990. pp. 19-22.
Marsland, R.A. et al "130 GHz GaAs Monolithic Integrated Circuit Sampling Head" Applied Physics Letters, vol. 55, No. 6, pp. 592-594, Aug. 1989.
Ricketts, David S. et al "A Chip-Scale Electrical Soliton Modelocked Oscillator", IEEE International Solid-State Circuits Conference, 2006.

* cited by examiner

DEVICE FOR ANALYZING A SAMPLE USING RADIATION IN THE TERAHERTZ FREQUENCY RANGE

FIELD OF INVENTION

The invention relates to a device for analyzing a sample using radiation in the terahertz frequency range.

BACKGROUND OF THE INVENTION

Spectroscopy devices are today widely used in commercial and scientific applications to identify and analyze substances of different kinds. In a typical spectroscopy device, a probe signal is sent to a sample and the reflected or transmitted part of the signal is then analyzed to capture the characteristic spectrum of the substance under test. The probe signal is in general electromagnetic radiation in the frequency range of infrared, visible light or microwave but also electrons or phonons can be used. The choice of the probe signal is related to the material properties that shall be investigated.

Recently, terahertz (THz) radiation (a range located between the microwaves and infrared light in the electromagnetic spectrum) has attracted the interest of the scientific and engineering community for its wide range of possible scientific and commercial applications. The fact that the vibrational modes of several molecules lie in this part of the spectrum and that water very easily blocks electromagnetic waves with those frequencies make THz radiation a suitable probe to investigate material properties which are usually not accessible with infrared probe signals or other types of probe signals.

Technical difficulties related to the possibility to detect and generate THz signals have for long time hindered the development of complete THz spectrometers, but nowadays several groups in the world have demonstrated the possibility to use THz radiation in such a way and even several commercial THz imaging and spectroscopic devices are available.

State-of-the-art THz spectroscopy devices are based on femto-second laser sources able to generate short light pulses to excite a Gallium Arsenide THz emitter. The generated THz radiation is sent toward a sample and the transmitted or reflected signal is then sampled using again the laser pulse. A schematic of transmission (FIG. 1) and reflection (FIG. 2) spectrometers operating according to this principle is shown in FIG. 1 and in FIG. 2, respectively. FIG. 1 shows a femto-second laser 200, a scanning optical delay line 201, a terahertz transmitter 202, a plurality of parabolic mirrors 203, a sample 204, a terahertz detector 205, a current pre-amplifier 206, and an A/D converter and DSP (digital signal processing) unit 207. FIG. 2 shows a similar arrangement in reflection geometry. A device of this type is described in U.S. Pat. No. 6,747,736.

Other devices to carry out spectroscopy in such frequency band use backward wave oscillators (BWO).

Both solutions are based on discrete and bulky components. BWOs are considered very inefficient in the interesting frequency range and femto-second lasers remain both very bulky and expensive.

A different approach to the problem which is described in "All-electronic terahertz spectroscopy device with terahertz free-space pulses" (by J. S. Bostak et al. in J. Opt. Soc. Am. B, 11, No. 12, December 1994) uses non-linear transmission lines for the generation of very short pulses with spectral content reaching the THz range. A schematic of such an all-electronic spectroscopy device is shown in FIG. 3. As the devices described above, also this electronic THz spectrometer is based on discrete and thus rather bulky components. A signal at 6.0 GHz is generated by an external synthesizer 100 and amplified by a 30 dBm amplifier 103 before reaching a non-linear transmission line 106 integrated with an antenna. The source signal at 6.0 GHz is compressed by the non linear transmission line 106 to a THz pulse and transmitted by the antenna. The beam is collected and focused by a silicon lens and focused again by an external paraboloidal mirror 108. A similar arrangement is present at the receiver side (including another external paraboloidal mirror 108), where the detector is composed by an all-electronic two-diode sampler driven by the signal to be sampled and the signal from another external synthesizer 101 amplified by a 30 dBm amplifier 104 compressed by a non-linear transmission line 107. The IF signal (intermediate frequency signal) generated in this way is amplified (by low-noise amplifier 110) and visualized on an external instrument 109 (which can e.g. be formed by a spectrum analyzer or oscilloscope). A mixer 105 is provided outputting a trigger signal to the external instrument 109. A 10 MHz reference clock 102 for phase lock is provided by the external synthesizer 100 to the other external synthesizer 101. The functioning of this device is described in the cited reference. As for the approaches described above (the one based on lasers and the other based on backward-wave oscillators), this device is also based on several discrete components and makes use of two or three external measurement instruments. As a consequence, it is not suited for widespread, low-cost commercial applications.

From JP 2007-078 621, a sensing device for acquiring information on a specimen near an electric conductor section using surface plasmon resonance is known. Laser light is used for generating and coupling an electromagnetic wave including a THz frequency region and coupling the electromagnetic wave to the electric conductor section.

From WO 2008/105888, a sensing system is known that includes a radiation source and an integrated sensing probe disposed adjacent to the radiation source. The radiation source is for example a terahertz radiation source. The integrated sensing probe includes a substrate, a corrugated reflective surface and a coaxial wave-guide structure having a coaxial wave-guide tip. The corrugated reflector surface functions to enhance transmittance of the radiation through the tip by coupling the radiation to surface plasmon polaritons. A detection system, which can include collection optics, can be positioned below a sample in case of a partially transparent sample substrate, or beside the sample to measure scattered signals, or above the sample on the substrate side to measure reflected radiation, or it can be coupled to the resonator above the waveguide tip to measure the detuning of the resonance by the waveguide tip.

From WO2006/123153, a wave-guide structure for terahertz radiation is known, in which the surface-plasmon concept is applied for all-optical terahertz generation. A femto second pulsed laser beam is used for generating terahertz radiation. The terahertz radiation propagates along an interface of the wave-guide structure by means of a surface plasmon. An evanescent wave has a tail into air, which can be used for detecting or sensing a gas or a biomedical substance.

SUMMARY OF THE INVENTION

It is an object of the invention to provide a device for analyzing a sample using radiation in the terahertz frequency range suitable for widespread, low-cost commercial applications. Further, this device shall have increased sensitivity.

This object is achieved by a device for analyzing a sample using radiation in the terahertz frequency range according to claim 1. The device comprises:—a transmitter comprising a THz signal generator for generating an electromagnetic THz signal, the THz signal generator comprising a nonlinear transmission line; and—a surface plasmon polariton generating unit adapted to convert the THz signal into a surface plasmon polariton. The transmitter and the surface plasmon polariton generating unit are either integrated on one common substrate or on two separate substrates. In the device the transmitter with the THz signal generator and the surface plasmon polariton generating unit are integrated either on one common substrate or on two separate substrates. Thus, all components for generating THz surface plasmon polaritons are integrated on the substrate or substrates, respectively, and the device is provided in a very compact way suited for low-cost commercial applications. Preferably, the substrate is a semiconductor substrate or, in case of two substrates, the substrates are semiconductor substrates. For example, one substrate can comprise the THz active part, i.e. the nonlinear transmission line(s) (NLTL) and oscillator(s), and a second (lower cost) substrate can comprise the plasmon part. Also this solution allows a very compact, integrated form suited for low-cost commercial applications. Since surface plasmon polaritons are exploited, increased sensitivity for analyzing a sample is achieved. Exploiting the nonlinear transmission line allows reliably achieving the desired THz frequency spectrum.

Preferably, the surface plasmon polariton generating unit comprises at least one radiating element and at least one directivity creating structure. For example, the radiating element can be formed by an antenna-like structure. In this case, surface plasmon polaritons with satisfactory directivity can be created and the device can be optimized such that most of the radiation power is diverted from free-space radiation into the surface waves. For example, suitable radiation elements are microstrip (patch) antennas or slot (aperture) antennas. It has been found that these types of antennas can launch surface waves over a wide range of operating frequencies in the same way as the edge of parallel-plate wave-guides acts. Power can be directed in a specific direction along the substrate by the directivity creating structure which can be formed by a reflector, a cavity, specific shaping of the radiating element, or by an appropriately arranged array of radiating elements. The surface plasmon polariton generating unit can for instance be integrated using the standard metal stack of a semiconductor process technology. However, the surface plasmon polariton generating unit can e.g. consist of additional metals, semiconductors and/or dielectrics (e.g. organic dielectric layers, copper or aluminum) which are post-processed to the surface of a substrate formed by a semiconductor chip. It should be noted that a thicker dielectric layer and a higher dielectric constant will couple more energy into the THz surface plasmon polariton while optimizing the coupling efficiency of the surface plasmon generating unit.

The device further comprises a THz surface plasmon polariton sensor adapted for bringing generated surface plasmon polaritons in interaction with a sample. In case of two substrates, the THz surface plasmon polariton sensor is preferably integrated on the same substrate with the surface plasmon polariton generating unit. In this case, the sensor which is adapted for actually sensing properties of a sample to be analyzed is also comprised on the substrate or the substrates, respectively, and thus in a very compact way. The surface plasmon polariton sensor can be formed by a conductive surface layer on which a propagating surface plasmon polariton or a localized surface plasmon polariton can be excited. The material of the THz surface plasmon polariton sensor can be e.g. a metal, or a doped or an undoped semiconductor with an appropriate charge carrier concentration. The conductive layer can e.g. be thick (i.e. much larger than the conductor skin depth) or thin (comparable to or smaller than the conductor skin depth). Several possibilities for achieving the desired sensitivity exist, for example by provision of a flat surface covered with a dielectric layer, by structuring the conductive surface with hole arrays to increase the effective skin depth of the conductor and field enhancement at the surface, or by structuring one or several waveguides onto the surface to manipulate the surface plasmon polariton propagation and increase its interaction with the sample to be analyzed. Another example can e.g. be the provision of periodic or complex surface structures which lead to resonant scattering of THz surface plasmon polaritons and increase their interaction with the sample to be analyzed by means of, for instance, slowing-down of the surface plasmon polariton propagation or localizing surface plasmon polaritons in resonant structures.

The device further comprises a receiver comprising a THz surface plasmon polariton detector adapted for converting surface plasmon polaritons into an electromagnetic THz signal. Also the receiver of the device for analyzing a sample using radiation in the terahertz frequency range is comprised on the substrate or one of the substrates, respectively. Thus, a fully integrated device is provided which is particularly suited for widespread, low-cost commercial applications. As in the transmitter, the THz active part may be integrated on a different substrate than the passive plasmonic part, with the two substrates closely placed together. The THz surface plasmon polariton detector can e.g. be formed similar to the surface plasmon polariton generating unit (but functioning in the opposite way by converting surface plasmon polaritons into an electromagnetic THz signal). According to an aspect, the surface plasmon polariton detector comprises at least one antenna, e.g. similar to the antenna of the surface plasmon polariton generating unit as described above.

Preferably, the receiver comprises a nonlinear transmission line. In this case, the signal can be reliably detected. If the receiver comprises a two-diode sampling bridge, the received signal can be reliably sampled using a locally generated pulse or shock.

Preferably, both the transmitter and the receiver comprise at least one oscillator each. Another possibility is that one of the signals generated by two oscillators located in the transmitter (receiver) is used in the receiver (transmitter).

According to an aspect, the THz signal generator is adapted such that the electromagnetic THz signal is a shock or pulse. Thus, the desired electromagnetic THz signal can be conveniently generated using an oscillator, an amplifier, and a nonlinear transmission line, or using a soliton oscillator. In one implementation, the THz signal generator is a soliton oscillator, the soliton oscillator comprising an amplifier and a nonlinear transmission line in a feedback loop of the amplifier. It has been shown that such an implementation is capable of providing pulses with full width at half maximum (FWHM) of 293 ps and shows promise for lower FWHM down to 1 ps.

Preferably, the device further comprises an analog low-frequency IF output. In this case, the sensed signal is output for further analysis through the analog low-frequency IF (intermediate frequency) output. Since the IF output signal is a low-frequency signal, it can conveniently be analyzed with conventional techniques. Analysis can be performed in another chip which can e.g. be realized in CMOS technology. If the device further comprises an analog-digital converter and a digital signal processing unit, the analysis can be performed in the device and both sensing and analysis are realized in a space-saving manner.

According to one aspect, the device is an imaging device or a spectroscopy device, preferably a medical image acquisition device or a medical spectroscopy device. The possible applications of this invention are in the domain of spectrometry in the THz band. This is a relatively new field, but several applications in medicine and biology are already known. Moreover, commercial applications are already available but the size and cost of nowadays instruments hinder a more widespread use of such a technique. With this invention, THz spectrometry becomes a reliable, low-cost truly mobile technology. Low cost, fully integrated THz spectrometers could become available for widespread use in medicine and biology for substance identification and analysis. Such low-cost spectrometers could be provided to any policeman for illicit drugs detection or to detect specific substances in any customs office. Also in airports, inoffensive substances such as talcum powder could be distinguished from other, forbidden substances. Also applications in the pharmaceutical industry are possible. In this field, a commercial application is already available for distinguishing two polymorphs of the same drug in an undisruptive way using THz spectrometry with a large reduction of costs for pharmaceutical companies. The device might also be used for imaging biological tissue, such as human skin in order to for instance detect skin diseases.

It should be noted that throughout the specification the terms "electromagnetic THz radiation" and "electromagnetic THz signal" are used to describe both free-space THz radiation and guided wave THz radiation (and a corresponding signal, respectively). In contrast, (THz) surface plasmon polaritons shall not be covered by this term and will be explicitly named surface plasmon polaritons.

BRIEF DESCRIPTION OF THE DRAWINGS

Further features and advantages of the present invention will arise from the detailed description of embodiments with reference to the enclosed drawings.

DETAILED DESCRIPTION OF EMBODIMENTS

First Embodiment

Figure 4:
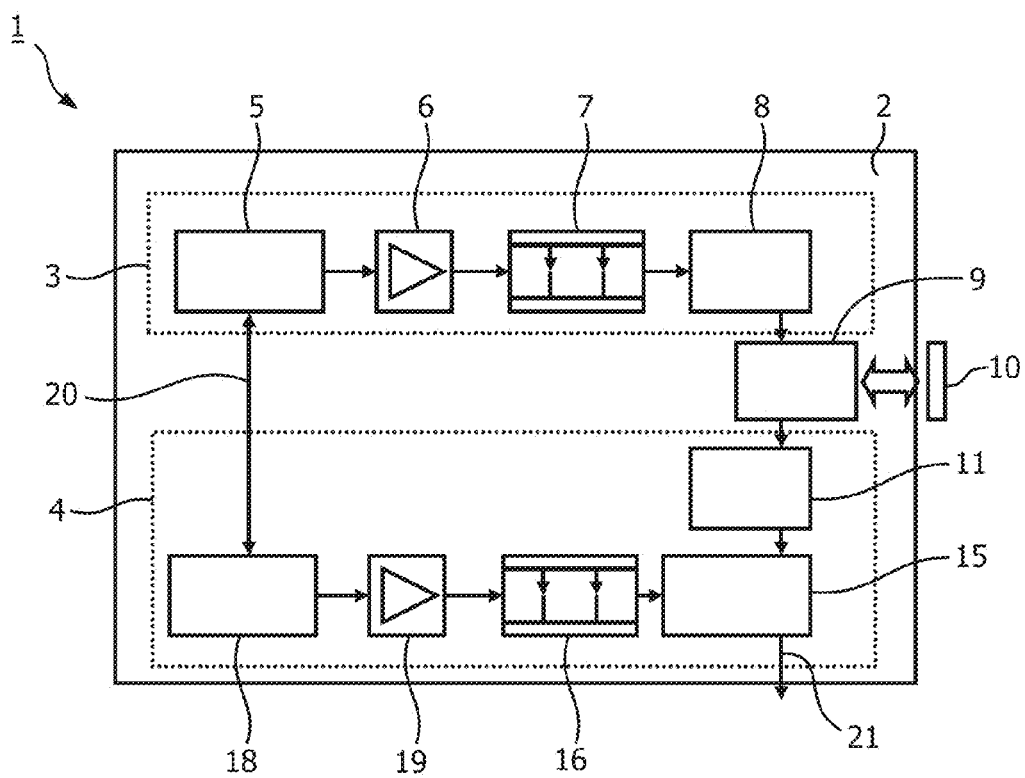
FIG. 4 schematically shows a device for analyzing a sample using radiation in the terahertz frequency range according to a first embodiment.

A first embodiment of the present invention will now be described with reference to FIG. 4. The device for analyzing a sample using radiation in the terahertz frequency range schematically shown in FIG. 4 is a fully-integrated THz imaging/spectroscopy device, in particular a fully-integrated lab-on-chip terahertz spectroscopy device.

In the embodiment, all components of the device for analyzing a sample using radiation in the terahertz frequency range are integrated on a semiconductor substrate 2 (semiconductor chip). With nowadays technology, Gallium Arsenide (GaAs) seems to be the most suitable semiconductor to be used for the implementation of the device, so in the rest of the document a GaAs substrate will be considered as the semiconductor substrate 2, but other materials like Silicon could be used in the future if their performance will be good enough. As an alternative, and to reduce cost, two substrates could be used, one for the active part (oscillators and nonlinear transmission lines) and one, with lower cost, for the passive part (the surface plasmon polariton generating unit and the surface plasmon polariton sensor).

Figure 1:
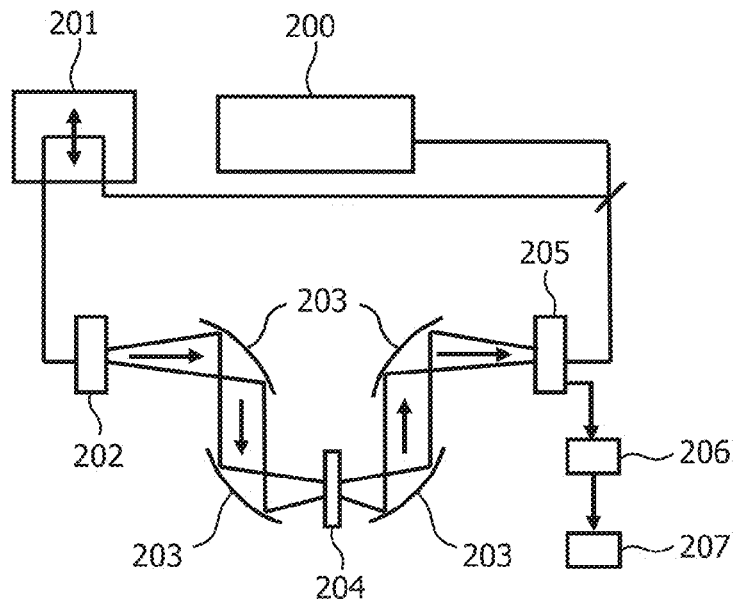
FIG. 1 shows a prior art THz transmission spectroscopy device.
Figure 2:
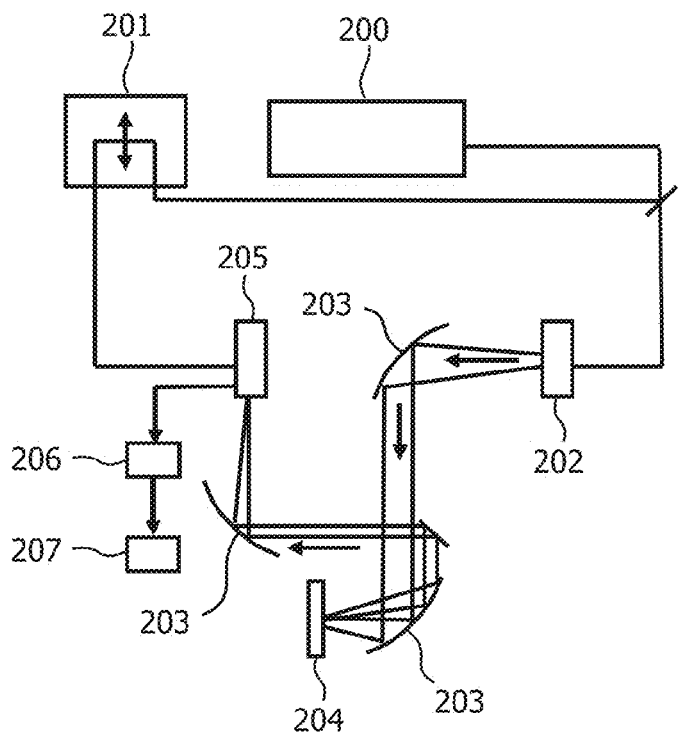
FIG. 2 shows a prior art THz reflection spectroscopy device.
Figure 3:
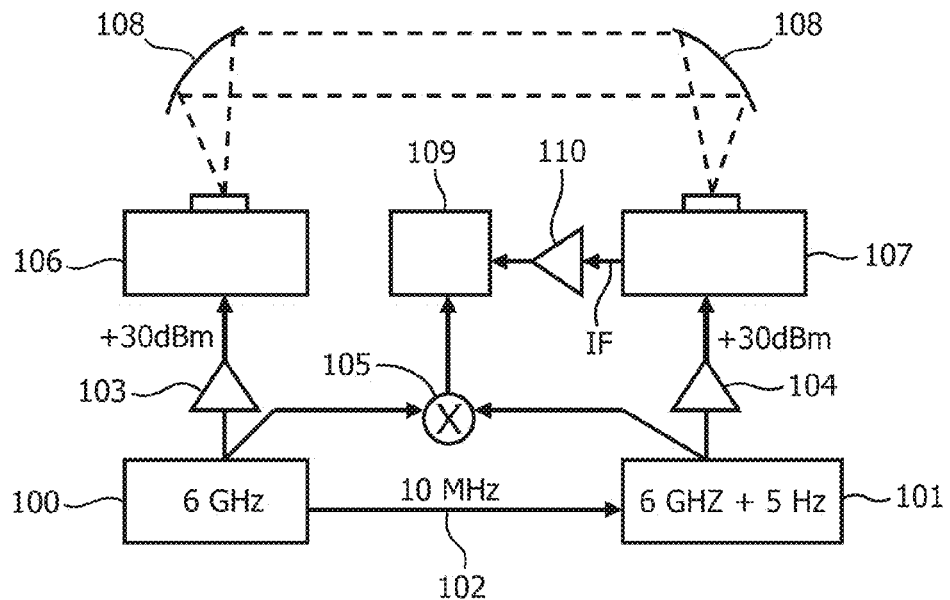
FIG. 3 shows an all-electronic discrete spectroscopy device based on non-linear transmission lines.

The chip is composed by a transmitting part (transmitter) 3 and a receiving part (receiver) 4, both integrated on the semiconductor substrate 2. The chip is provided with a plastic package in order to prevent damaging of the chip. The working principle of the transmitting and receiving parts corresponds partly to the one described in "All-electronic terahertz spectroscopy device with terahertz free-space pulses" (see above) and shown in FIG. 3. However, in the imaging/spectroscopy device 1 according to the embodiment all the components are integrated on the semiconductor substrate 2 (or on two, closely spaced, substrates) and surface plasmon polaritons are exploited for sensing properties of a sample which enables achieving higher sensitivity.

First, the transmitting path in the transmitting part 3 will be described. An oscillator 5 composed of standard transistors in GaAs or other suitable semiconductor technology generates a sinusoidal microwave signal of, for example, 6 GHz. An amplifier 6 is used to bring the level of the signal to suitable power. A nonlinear transmission line 7 is used to compress the input sinusoidal signal into an electromagnetic THz signal (shockwave) with very wide spectral content (up to 1 THz or more). The oscillator 5, the amplifier 6, and the non-linear transmission line 7 together form a THz signal generator. From this point on, the frequencies involved are so high that no other operation on the signal is possible with standard semiconductor transistors. The non-linear transmission line 7 is composed by a linear coplanar waveguide or other suitable transmission line structure periodically loaded by nonlinear capacitances, as for example reverse-biased Schottky diodes. The non-linear capacitances are responsible for the formation of shockwaves (with wide spectral content). The formation of such shock waves is e.g. described in "Delta-doped Schottky diode nonlinear transmission lines for 480 fs 3.5-V transients" (by D. W. van der Weide; Appl. Phys. Lett. 65, pp 881-883, August 1994).

The generated shock waves are transmitted to a surface plasmon polariton generating unit 8 converting the electromagnetic THz shockwaves being an electromagnetic THz signal into a surface plasmon polariton. The surface plasmon polariton generating unit 8 will also be called SP converter which stands for shock/soliton-plasmon converter. The surface plasmon polariton generating unit 8 is a passive block used to convert the THz pulse into a THz surface plasmon polariton which is an electromagnetic wave coupled with the electronic oscillations at the interface between a conductor (e.g. a metal) and a dielectric. The SP converter which forms the surface plasmon polariton generating unit 8 in the embodiment consists of a radiating element (e.g. an antenna-like structure), a reflector or cavity creating directivity for its radiation (also referred to as a directivity creating structure), and a connection or transition to the surface plasmon polariton. The device for analyzing a sample using radiation in the terahertz frequency range 1 is optimized such that most of the radiation power is diverted from electromagnetic radiation into the surface waves, i.e. into the surface plasmon polaritons. The radiating element of the surface plasmon polariton generating unit 8 can e.g. be formed by one or more microstrip (patch) antenna(s) or by one or more slot (aperture) antenna(s). It has been shown that such antennas can launch surface waves over a wide range of operating frequencies. Power is directed in a specific direction along the substrate by a directivity creating structure which can e.g. be formed by a reflector, a cavity, appropriate shaping of the radiating element, or by an appropriately arranged array of radiating elements. For example, the SP converter can be integrated to the respective substrate using the standard metal stack of a semiconductor process technology. However, the SP converter can also comprise additional metals, semiconductor and/or dielectric layers such as organic dielectric layers, copper, and/or aluminium. For instance, these additional components can be post-processed to the surface of the semiconductor chip being the substrate.

The surface plasmon polariton generated by the surface plasmon polariton generating unit 8 is then transferred to a THz surface plasmon polariton sensor 9 adapted for bringing generated surface plasmon polaritons in interaction with a sample 10. The interaction between the surface plasmon polaritons and the sample 10 is schematically indicated by a double-arrow in FIG. 4. The THz surface plasmon polariton sensor 9 is the component of the device for analyzing a sample using radiation in the terahertz frequency range 1 at which the interaction between the probe signal (the surface plasmon polariton) and the sample 10 takes place. The THz surface plasmon polariton sensor 9 comprises a conductive surface on which a propagating surface plasmon polariton or a localized surface plasmon polariton (in the THz frequency range) can be excited. The surface plasmon polariton leads to an enhancement of the electromagnetic field amplitude at the surface and increased sensitivity.

In operation of the device, the sample 10 to be analyzed is brought close to the conductive surface of the surface plasmon polariton sensor 9 at the position in which the field amplitude is large. The occurring interaction between the surface plasmon polaritons and the sample 10 results in modifications to the surface plasmon polariton characteristics, e.g., the surface plasmon frequency or the surface plasmon life time, which can be detected and serve to analyze the properties of the sample 10.

The material of the surface plasmon polariton sensor 9 can for instance be a metal, a doped semiconductor, or an undoped semiconductor with an appropriate charge carrier concentration. There are different possibilities how the conductive surface of the surface plasmon polariton sensor 9 can be formed. For instance, the conductive layer can be thick (i.e. much larger than the conductor skin depth with respect to the THz frequency range) or thin (i.e. comparable to or smaller than the conductor skin depth). Several possibilities for enhancing the electromagnetic field confinement to the surface and for enhancing the sensitivity of the device exist.

For example, according to one example, it is possible to cover a flat surface with a dielectric layer. Such an arrangement is shown in "Time domain measurements of surface plasmon polaritons in the THz frequency domain" by J. Saxler et al. (Phys. Rev. B 69, 155427 (2004).

According to another example, the conductive surface can be structured with hole arrays in order to increase the effective skin depth of the conductor and the field enhancement at the surface, as proposed in "Mimicking surface plasmons with structured surfaces" by J. B. Pendry et al. in Science 305, 847 (2004).

According to a still further example, one or several waveguides can be structured onto the surface to manipulate the surface plasmon polariton propagation and increase its interaction with the sample 10.

Further examples comprise periodic or complex structures that lead to resonant scattering of THz surface plasmon polaritons and increase their interaction with the sample by means of e.g. slowing-down of the surface plasmon polariton propagation, as described in "Propagation of surface plasmon polaritons on semiconductor gratings" in Phys. Rev. Lett., 93, 256804 (2004) or by localizing surface plasmon polaritons in resonant structures.

The receiver path in the receiving part 4 works as follows: After interaction with the sample 10, the probe signal (i.e. the modified surface plasmon polaritons) is received by a further SP converter forming a THz surface plasmon polariton detector 11 being a part of the receiving part 4. The THz surface plasmon polariton detector 11 can be formed analogously to the THz surface plasmon polariton generating unit 8. The THz surface plasmon polariton detector 11 operates such that the surface plasmon polaritons are received, e.g. by an integrated antenna, and converted into electromagnetic radiation. In other words, the THz surface plasmon polariton detector 11 operates in the opposite way as compared to the surface plasmon polariton generating unit 8. The electromagnetic signal from the THz surface plasmon polariton detector 11 is then sampled using a two-diode sampling bridge 15 driven by a shockwave signal coming from another nonlinear transmission line (NLTL) 16. As for the transmitter part 3, the shockwave is generated compressing the sinusoidal signal coming from an integrated oscillator 18 and amplified by an amplifier 19. The diode sampling bridge 15 (which is a known component described in open literature (e.g. in "Monolithic integrated circuits for mm-wave instrumentation" by R. A. Marshland et al. in IEEE GaAs IC Symposium, October 1990; or in "130 GHz GaAs monolithic integrated circuit sampling head", Appl. Phys. Lett., 55, pp 592-594, August 1989)) uses the locally generated pulse to sample the received signal. The diode sampling bridge 15 is also integrated on the semiconductor substrate 2 (or on one of the substrates, in the case of the alternative). For instance, the transmitter and receiver oscillators 5, 18 can be phase locked as schematically indicated at 20. A low-frequency IF output 21 is provided on the semiconductor substrate 2 for further analysis which can e.g. be performed in another (for example CMOS) chip.

Second Embodiment

Figure 5:
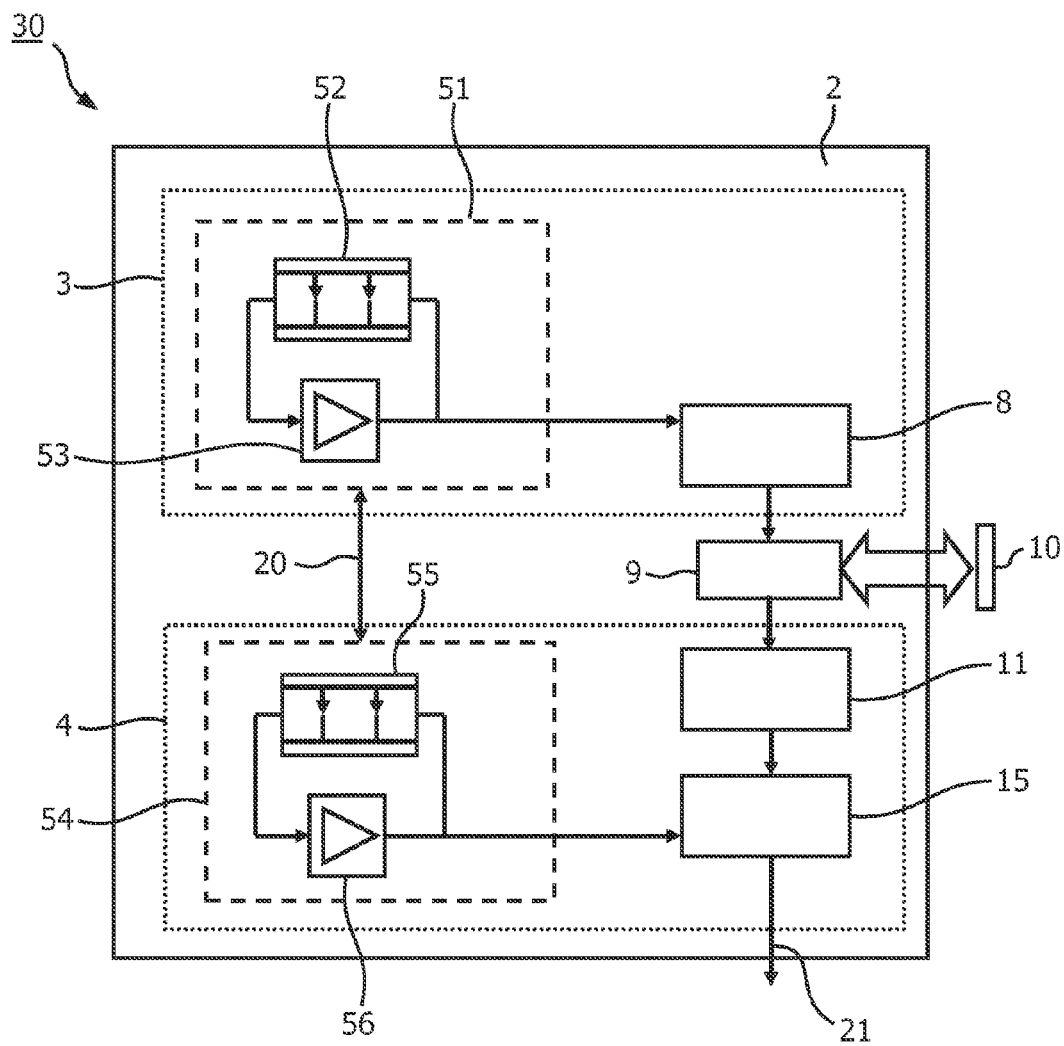
FIG. 5 schematically shows a device for analyzing a sample using radiation in the terahertz frequency range according to a second embodiment.

A second embodiment will now be described with respect to FIG. 5. In the device for analyzing a sample using radiation in the terahertz frequency range 30 according to the first embodiment, the THz pulses are generated from a shockwave created using the nonlinear transmission line. It should be noted that at least another method to generate wide-band short pulses is known and could be used in the device for analyzing a sample using radiation in the terahertz frequency range. This other method will be described with respect to the second embodiment.

The overall set-up of the second embodiment is based on the structure described above with respect to the first embodiment. Therefore, like components are denoted with like reference signs and their description will be omitted. However, the method to generate wide-band short pulses differs from the first embodiment. This method is based on the recently introduced soliton oscillator 51, composed by a special amplifier 53 with a nonlinear transmission line (NLTL) 52 in his feedback loop. Such an arrangement is disclosed in "A chip-scale electrical soliton modelocked oscillator" (by D. S. Ricketts, D. Ham in IEEE International Solid-State Circuits Conference, 2006). This circuit topology has been demonstrated to be able to generate pulses with full width at half maximum (FWHM) of 293 ps and shows promise for lower width down to 1 ps. Using the soliton oscillator the device for analyzing a sample using radiation in the terahertz frequency range is constructed as schematically shown in FIG. 5.

The transmitting part 3 comprises a soliton oscillator 51 comprising a nonlinear transmission line 52 and a special amplifier 53. In this embodiment, the soliton oscillator forms a THz signal generator.

Similarly, the receiving part 4 comprises a further soliton oscillator 54 comprising a further nonlinear transmission line 55 and a further special amplifier 56. For instance, the two soliton oscillators can be phase locked as schematically indicated by the double arrow 20. The working principle is similar to the one of the first embodiment, but here the electromagnetic signal input to the surface plasmon polariton generating unit 8 and the sample signal input to the sampling bridge 15 are the solitons generated by the soliton oscillators. Again, the THz active part and the plasmon part can be integrated on two different substrates which enables further cost reduction.

Both embodiments describe a sort of front-end for THz signal generation and detection. The intermediate frequency (IF) output 21 can be used as input of a CMOS circuit containing an A/D converter and a DSP (digital signal processing unit) for analysis of the results.

This device, composed essentially by only two chips (the THz front-end chip 1, 30 and the CMOS chip) could be a complete lab-on-chip THz spectrometer including data analysis and visualization on a suitable display. Compared to existing THz spectrometers, the proposed device is advantageous with respect to the size, the power consumption and the costs.

To summarize, a fully integrated device for analyzing a sample using radiation in the terahertz frequency range is provided which can e.g. serve as a fully integrated THz spectrometer. The device is based on non-linear transmission lines or the recently introduced soliton oscillator, a surface plasmon soliton generating unit converting a THz pulse into a THz surface plasmon polariton and a THz surface plasmon polariton sensor. In this device, all the elements to generate and detect the THz radiation and the surface plasmon polariton are integrated on one microchip or two microchips closely placed together (made for example of Gallium Arsenide or another suitable semiconductor) and packaged into a lab-on-chip form.

Thus, in both embodiments, the device comprises the following features:
Non-linear transmission lines for the generation of THz pulses;
A surface plasmon polariton generating unit (a SP converter) used to transform a THz signal (shock or soliton) into a surface plasmon polariton;
A THz surface plasmon polariton sensor; and
All the components are assembled together to form a lab-on-chip.

A fully integrated all-electronic lab-on-chip terahertz (THz) spectroscopic system is presented. In difference to existing THz spectrometers, this is a truly low-cost, mobile device which could allow a more widespread use of spectrometry in medical, biological and pharmaceutical laboratories. Use for security applications in airports or other sensitive locations is also possible. Considering the low cost and the simplicity of use, new applications in consumer electronics can also be introduced. Moreover, the THz front-end could be used as a fundamental building block for new, safe imaging tools. As opposite to current THz devices based on laser or tube devices, the proposed device is fully integrated and electronic; it is based on nonlinear transmission lines or the recently introduced soliton oscillator.

Although conversion of free-space electromagnetic radiation to surface plasmon polaritons and vice versa has been described above, it should be noted that the invention is not limited to this and also conversion of guided wave radiation to surface plasmon polaritons and vice versa shall be covered.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements, and by means of a suitably programmed computer. In the device claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. Device for analyzing a sample using radiation in the terahertz frequency range, comprising:
   a transmitter comprising a THz signal generator for generating an electromagnetic THz signal, the THz signal generator comprising a nonlinear transmission line;
   a surface plasmon polariton generating unit adapted to convert the THz signal into a surface plasmon polariton;
   a THz surface plasmon polariton sensor adapted for bringing generated surface plasmon polaritons in interaction with a sample; and
   a receiver comprising a THz surface plasmon polariton detector adapted for converting surface plasmon polaritons into an electromagnetic THz signal;
   the transmitter, the surface plasmon polariton generating unit, and the receiver being either integrated on one common substrate or on two separate substrates; wherein all components for generating THz surface plasmon polaritons are integrated on said substrate or substrates, respectively.

2. Device according to claim 1, wherein the surface plasmon polariton generating unit comprises at least one radiating element and at least one directivity creating structure.

3. Device according to claim 1, wherein the THz surface plasmon polariton sensor comprises a conductive surface adapted such that a propagating surface plasmon polariton or a localized surface plasmon polariton can be excited.

4. Device according to claim 1, wherein the surface plasmon polariton detector comprises at least one antenna.

5. Device according to claim 1, wherein the receiver comprises a nonlinear transmission line.

6. Device according to claim 1, wherein the receiver comprises a two-diode sampling bridge.

7. Device according to claim 1, wherein both the transmitter and the receiver comprise at least one oscillator each.

8. Device according to claim 1, wherein the THz signal generator is adapted such that the electromagnetic THz signal is a shock or pulse.

9. Device according to claim 1, wherein the THz signal generator is a soliton oscillator, the soliton oscillator comprising an amplifier and a nonlinear transmission line in a feedback loop of the amplifier.

10. Device according to claim 1, wherein the device further comprises an analog low-frequency IF output.

11. Device according to claim 1, wherein the device further comprises an analog-digital converter and a digital signal processing unit.

12. Device according to claim 1, wherein the device is an imaging device or a spectroscopy device.

13. Device according to claim 1, wherein the device is a medical image acquisition device or a medical spectroscopy device.

* * * * *